United States Patent
Laurent et al.

(10) Patent No.: US 11,701,319 B2
(45) Date of Patent: Jul. 18, 2023

(54) RHEOFLUIDIFYING CONCENTRATED FOAMING COMPOSITION AND USES OF SAME, IN PARTICULAR FOR BODY HYGIENE

(71) Applicant: LABORATOIRES DE BIOLOGIE VEGETALE YVES ROCHER, La Gacilly (FR)

(72) Inventors: Marie-Agnès Laurent, Bretigny sur Orge (FR); Estelle Bouvet, Le Mans (FR)

(73) Assignee: LABORATOIRES DE BIOLOGIE VEGETALE YVES ROCHER, La Gacilly (FR)

( * ) Notice: Subject to any disclaimer, the term of this patent is extended or adjusted under 35 U.S.C. 154(b) by 95 days.

(21) Appl. No.: 16/314,604

(22) PCT Filed: Jun. 30, 2017

(86) PCT No.: PCT/FR2017/051776
§ 371 (c)(1),
(2) Date: Dec. 31, 2018

(87) PCT Pub. No.: WO2018/002557
PCT Pub. Date: Jan. 4, 2018

(65) Prior Publication Data
US 2019/0314258 A1  Oct. 17, 2019

(30) Foreign Application Priority Data
Jul. 1, 2016 (FR) ...................................... 1656329

(51) Int. Cl.
| | |
|---|---|
| *A61K 8/60* | (2006.01) |
| *A61K 8/02* | (2006.01) |
| *A61K 8/04* | (2006.01) |
| *A61K 8/41* | (2006.01) |
| *A61K 8/44* | (2006.01) |
| *A61K 8/46* | (2006.01) |
| *A61K 8/55* | (2006.01) |
| *A61Q 5/02* | (2006.01) |
| *A61Q 19/10* | (2006.01) |

(52) U.S. Cl.
CPC ............ *A61K 8/604* (2013.01); *A61K 8/0295* (2013.01); *A61K 8/042* (2013.01); *A61K 8/416* (2013.01); *A61K 8/442* (2013.01); *A61K 8/463* (2013.01); *A61K 8/55* (2013.01); *A61Q 5/02* (2013.01); *A61Q 19/10* (2013.01); *A61K 2800/30* (2013.01); *A61K 2800/596* (2013.01)

(58) Field of Classification Search
CPC ........ A61K 8/604; A61K 8/042; A61K 8/416; A61K 8/442; A61K 8/463; A61K 8/55; A61K 2800/30; A61K 2800/596; A61Q 5/02; A61Q 19/10
See application file for complete search history.

(56) References Cited

U.S. PATENT DOCUMENTS

| | | | |
|---|---|---|---|
| 5,925,615 A | * | 7/1999 | Kern .................... A61K 8/9794 510/463 |
| 2005/0090422 A1 | | 4/2005 | Lukenbach |
| 2012/0183591 A1 | | 7/2012 | Dahms |
| 2014/0162979 A1 | | 6/2014 | Palla-Venkata |

FOREIGN PATENT DOCUMENTS

WO          9416680 A1    8/1994

OTHER PUBLICATIONS

T. Sakai, "Body Care Cosmetics", Cosmetic Science and Technology: Theoretical Principles and Applications. Netherlands: Elsevier Science, 2017, Chapter 33, 561-570. (Year: 2017).*
International Search Report for corresponding application PCT/FR2017/051776 filed on Jun. 30, 2017; dated Oct. 25, 2017.

* cited by examiner

*Primary Examiner* — Mina Haghighatian
*Assistant Examiner* — Nathan W Schlientz
(74) *Attorney, Agent, or Firm* — ArentFox Schiff LLP (57) ABSTRACT

A rheofluidifying surfactant composition structured into planar lamellar phases includes: a) at least one anionic surfactant and b) at least one compound selected from among amphoteric surfactants and non-ionic surfactants, in which the total active material of said surfactants is between 35 and 60% by weight relative to the total weight of said composition, in which the ratio of anionic surfactant is between 0.3 and 0.9, the ratio of amphoteric surfactant is between 0.0 and 0.7 and the ratio of non-ionic surfactant is between 0.0 and 0.7, said ratio being the ratio between the weight percentage of active material of said surfactant in said composition and the weight percentage of total active material of said surfactants in said composition, the pH of the composition being between 4 and 8, said at least one anionic surfactant being selected from the group comprising alkyl sulfates, alkyl ether sulfates, sulfonates, derivatives of phosphoric acid, phosphates and alkyl phosphates, isethionates, taurates, sulfoccinates, alkyl sulfoacetates, anionic derivatives of proteins of plant origin, amino acids and amino acid derivatives, polypeptides, carboxylic acids and the salts of same, salts of fatty acids from saponification, lactic acid derivatives and alkyl polyglucoside derivatives, and said composition being free of sodium chloride other than that which may be provided by the surfactants.

13 Claims, 2 Drawing Sheets

RHEOFLUIDIFYING CONCENTRATED FOAMING COMPOSITION AND USES OF SAME, IN PARTICULAR FOR BODY HYGIENE

TECHNICAL FIELD

The present disclosure relates to a surfactant composition comprising at least one anionic surfactant and at least one compound chosen from amphoteric surfactants and nonionic surfactants, and also to a cosmetic or dermatological composition comprising a surfactant composition of the disclosure.

The present disclosure has applications in particular in the field of cosmetics.

BACKGROUND

During the last thirty years, the use of shower gels has gradually become a daily act during washing and dressing, due to the pleasant sensation which they provide on the skin, their varied fragrances and their practicality of use.

Shower gels are generally packaged in bottles, optionally provided with a pump, or in flexible tubes. They are generally formulated in order to have a viscosity, being provided in the gel form, in order to allow them to dispense either by pouring from a bottle, or by pressing a flexible tube or by pressure exerted on the pump of a pump-action bottle. The gel is generally diluted with water at the time of application to the skin, which also makes possible the formation of foam during the massaging or the friction of the product with the skin.

However, environmental concerns are assuming growing importance in the cosmetics field. As a conventional shower gel contains at least 85% of water, there is currently a search, for ecological reasons, to reduce the amount of water in cosmetic products of this type, in order, on the one hand, to reduce the amount of water transported and, on the other hand, to reduce the amounts of packaging.

Thus, one of the means for reducing the amount of water in cosmetic products is to concentrate them.

Concentrated body hygiene products exist on the market, even if they are much less widespread than in the field of detergency (washing powders, concentrated washing-up liquids, and the like).

In the 1990s, the Gühl brand provided a range of concentrated transparent shampoos in a bottle with a service cap.

The limit of these products relates to their application. This is because it is difficult to spray a very small amount of product over a large surface, which difficulty increases as the viscosity of the product increases. This delays the dilution of the product with water and thus the appearance of the foam.

There thus exists a real need for body hygiene products which overcome these failings, disadvantages and obstacles of the prior art, in particular for a process which makes it possible to control the water content of these products, so as to improve their environmental impact.

DESCRIPTION OF THE DISCLOSURE

After much research, the applicant company has succeeded in developing a body hygiene product, in particular for the skin and hair, which exactly meets these needs by providing a shear-thinning composition concentrated in surfactants.

This composition, which exhibits the viscosity of a shower gel, additionally has the property of fluidifying on spreading. The rheological properties of the composition according to the disclosure not only make possible easy spreading over the skin and/or hair but also make it possible to dispense the composition by a spray-generating device, if this is desired by the user.

Advantageously, the diffusion as a spray further improves the distribution of the composition over the body and the rate of dilution with water, to make possible rapid foaming. Furthermore, the low viscosity of the formulation makes possible complete use of the concentrated product: very little product remains in the plastic bottle at the end of use: the degree of release is optimal.

Advantageously, the composition according to the disclosure is at least approximately 4 times concentrated in surfactants, that is to say in foaming active material, with respect to a conventional shower gel, more widely between 3 and 5 or more widely still between 3 and 6.

The composition of the disclosure thus exhibits the advantage of being more ecological than the body hygiene products of the type of existing gels, since they can be provided in a smaller format.

Furthermore, the composition of the disclosure makes it possible to do without a preservative, for an advantage of harmlessness for the consumer and in order to reduce the impact on the environment.

As a result if its higher concentration than that of the body hygiene products of the type of existing gels, the volumes of products transported are reduced fourfold, which lowers in proportion the emissions of $CO_2$ during the transportation and by approximately 40% to 50% emissions of greenhouse gases.

The reduction in the volumes manufactured also makes it possible to reduce the capacities for storage of the products by a factor of 4.

As the packagings are smaller with respect to a conventional product, the applicant company estimates that the consumption of plastic in this context is reduced by approximately 50%, with respect to conventional products of the same range.

As a result of this smaller format, the body hygiene product resulting from the disclosure is more practical to use as it is lighter and more transportable. It can in this context be more easily used in the context of a journey or of a use outside the house, such as sporting activities.

Furthermore, it exhibits the same advantages as a conventional shower gel. It exhibits in particular a viscosity comparable to conventional foaming hygiene products and a good stability over time. Furthermore, the application of the hygiene product to wet skin or hair produces a pleasant foam, such as that formed by a conventional shower gel.

The applicant company has demonstrated that the shear-thinning properties of the composition of the disclosure are related to its physicochemical structure.

Without wishing to be committed to a specific mechanism of action, the applicant company has demonstrated that the composition of the disclosure is a "structured" surface-active medium. In other words, the surfactants present in the composition are arranged in a lyotropic phase of liquid crystal type, also known as mesophase. The phase is optically anisotropic and appears birefringent when it is observed in polarized light with an optical microscope. More specifically, it is a lamellar phase, where the surfactants are arranged in planar bilayers, also known as lamellae. The bilayers form a periodic stack, being separated from one another by intermediate layers of water.

Thus, a first subject matter of the disclosure relates to a surfactant composition comprising:
  a. at least one anionic surfactant, and
  b. at least one compound chosen from amphoteric surfactants and nonionic surfactants, in which the total active material of the surfactants is from 25% to 60% by weight, with respect to the total weight of the composition,
in which the ratio of anionic surfactant is from 0.3 to 0.9, the ratio of amphoteric surfactant is from 0.0 to 0.7 and the ratio of nonionic surfactant is from 0.0 to 0.7, the ratio being the ratio of the percentage by weight of active material of the surfactant in the composition to the percentage by weight of total active material of the surfactants in said composition, the pH of the composition being between 4 and 8.

"Active material" is understood to mean, within the meaning of the present disclosure, the surfactant present in the commercial starting material containing the surfactant. The active material is thus the cause of the surface-active properties of the starting material containing the surfactant. The starting material, generally distributed by a supplier, contains other components in addition to the active material having the surface-active properties, such as, for example, water or solvents, reaction residues and secondary products. The percentage of active material in a starting material is obtained by subtracting the percentage of water or solvent, the reaction residues and the secondary products present in the starting material in order to count only the percentage of the surfactant.

"Total active material" is understood to mean, within the meaning of the present disclosure, the sum of the active materials present in each starting material containing each surfactant and included in the surfactant composition of the disclosure.

According to the disclosure, the total active material of the surfactants can be from 25% to 60% by weight, with respect to the total weight of the composition, for example from 25% to 55%, or from 35% to 55%, or from 35% to 60%, or from 30% to 50%, or from 35% to 45%.

The composition of the disclosure has a pH of from 4.0 to 8.0, the limits being included. The pH can, for example, be from 4.5 to 7.5, or between 5.0 and 7.0, or between 5.5 and 6.5, the limits being included. Advantageously, the pH can be a physiological pH of between 5.0 and 6.0, the limits being included.

Advantageously, the surfactant composition does not contain sodium chloride other than that which may be contributed by the surfactants. This is because sodium chloride as such is not added during the preparation of the surfactant composition of the disclosure. However, the surfactant compositions forming part of the composition may contain some, which implies that a small amount of that sodium chloride may possibly be detected, in particular in the trace form, in the surfactant composition of the disclosure. There may, for example, be from approximately 0.005% to approximately 7.0% by weight of sodium chloride coming from the surfactant compositions, with respect to the total weight of said composition, for example between 0.05% and 6.0%, for example strictly of less than 2.0%, or strictly of less than 3.0%, or strictly of less than 4.0%, or strictly of less than 5.0%. There may more particularly be from approximately 0.1% to 5.0%, or from approximately 0.1% to 4.0%, or from approximately 0.5% to 4.0%, or from approximately 1.0% to 3.0%, or from approximately 1.0% to 4.0%, or from approximately 1.0% to 6.5%, or from approximately 2.0% to 6.0%. The absence of additional sodium chloride advantageously confers a better harmlessness on the composition, with respect to the conventional products to which sodium chloride is added.

Advantageously, the surfactant composition of the disclosure exhibits a good flow. This good flow is generally reflected by a good shear-thinning, that is to say a fall in viscosity of the values at low shear (approximately $1\ s^{-1}$), which can, for example, be between 0.5 and 20 Pa·s, toward low viscosity values at high shear (approximately $150\ s^{-1}$), which can, for example, be between 0.01 and 1 Pa·s.

Advantageously, the surfactant composition of the disclosure exhibits a good sprayability. The latter can be reflected by a low viscosity value at high shear and a low value of the yield point (for example with a yield point $\tau 0 < 7$ Pa), preferably with values of approximately 3 Pa.

The rheology of the surfactant composition can be measured by any method known to a person skilled in the art, for example by controlled stress flow measurement, for example using a Thermo Fisher RS 600 controlled-stress rotational rheometer.

Particularly advantageously, the surfactant composition of the disclosure is devoid of preservative. In other words, the composition does not contain a preservative other than the components expressly mentioned as liable to form part of the surfactant composition of the disclosure, for example as surfactant or fragrance, and which might intrinsically exhibit preservation properties. This is because the surfactant composition has the advantage of exhibiting, without addition of dedicated preservative, a stability over time comparable to that of the conventional products, in particular those comprising preservatives. The surfactant composition of the disclosure additionally exhibits the advantage of avoiding the risks relating to the addition of preservatives, such as disturbances of the hormonal system, skin irritation or skin allergies. By way of example, the preservatives not used in the context of the surfactant composition of the disclosure are parabens, triclosan, methylisothiazolinone, formaldehyde releasers and phenoxyethanol, this list not being limiting, sodium benzoate, salicylic acid, sorbic acid.

The water is from 40% to 65% by weight, with respect to the total weight of the surfactant composition. For example, it can be from 50% to 60%. The surfactant composition of the disclosure thus exhibits a better environmental impact, with respect to a conventional product, owing to the fact that the reduction in the water content of the product makes it possible, on the one hand, to reduce the amount of water transported and, on the other hand, to reduce the amounts of packaging of the product, with respect to a conventional product comprising approximately 85% of water.

The composition of the disclosure can additionally comprise at least one fragrance. "Fragrance" is understood to mean, within the meaning of the present disclosure, a scenting starting material or a mixture of scenting starting materials, also known as "fragrance concentrate", of natural and/or synthetic origin, dissolved or not dissolved in a solvent for perfumery starting materials. In other words, it can be any scented composition or any mixture of scented starting materials exhibiting olfactory characteristics compatible with use in cosmetics, generally highly concentrated, generally provided packaged by a perfumer. The solvent can be any appropriate solvent known to a person skilled in the art, such as, for example, ethanol, dipropylene glycol, triethyl citrate, isopropyl myristate or triacetin, this list not being limiting. The starting materials of natural origin can be any appropriate starting material known to a person skilled in the art, for example essential oils, concretes, absolutes or plant extracts. The proportions between solvent and scented starting materials can be highly variable according to the olfactory power of the scented starting materials and their solubility, according to what is conventionally carried out in the field of fragrances, known to a person skilled in the art. According to the disclosure, the percentage by weight of fragrance in the composition contributes to the agreeableness of the composition and thus makes it possible to obtain a scenting power comparable to that of a conventional product. The fragrance can therefore be concentrated between 2 and 6 times, with respect to the concentration of a conventional product. For example, the concentration of fragrance can range from 0.05% to 10% by weight, with respect to the total weight of the composition, for example from 0.5% to 10%, or from 0.5% to 5.0%, or from 1.0% to 5.0%, or from 1% to 10%, or from 2% to 10%, or from 3% to 10%, or from 5% to 10%. The fragrance can be any commercial scenting composition, for example Parfum citron Basilic (Givaudan) or Parfum Baie acidulée (Robertet). Advantageously, the fragrance can result in a lowering of the viscosity of the surfactant mixture, in order to obtain a more fluid product, and/or in a lowering of the yield point of the composition, which improves the sprayability.

According to the disclosure, the surfactant composition comprises at least one compound chosen from amphoteric surfactants and nonionic surfactants. Thus, when the ratio of amphoteric surfactant is 0.0, the ratio of nonionic surfactant cannot be equal to 0.0; the value of 0.0 is thus excluded in this case. Conversely, when the ratio of nonionic surfactant is equal to 0.0, the ratio of amphoteric surfactant cannot be equal to 0.0; the value of 0.0 is thus excluded in this case.

According to the disclosure, the ratio of anionic surfactant is from 0.3 to 0.9, for example from 0.4 to 0.8, or from 0.5 to 0.7.

According to the disclosure, the ratio of amphoteric surfactant is from 0.0 to 0.7, for example from 0.1 to 0.6, or from 0.2 to 0.5.

According to the disclosure, the ratio of nonionic surfactant is from 0.0 to 0.7, for example from 0.1 to 0.6, or from 0.2 to 0.5.

For example, a surfactant composition according to the disclosure can consist of:
 a. at least one anionic surfactant, and
 b. at least one amphoteric surfactant and at least one nonionic surfactant,
in which the total active material of the surfactants is from 25% to 55% by weight, with respect to the total weight of the composition,
in which the ratio of anionic surfactant is from 0.3 to 0.9, the ratio of amphoteric surfactant is from 0.0 to 0.7, the value of 0.0 being excluded, and the ratio of nonionic surfactant is from 0.0 to 0.7, the value of 0.0 being excluded,
the pH of the composition being between 4 and 8.

In this case, no other compound than those indicated in this example is added to the composition of the disclosure.

According to another example, a surfactant composition according to the disclosure can comprise or consist of:
 a. at least one anionic surfactant, and
 b. at least one amphoteric surfactant and at least one nonionic surfactant,
in which the total active material of the surfactants is from 25% to 55% by weight, with respect to the total weight of the composition,
in which the ratio of anionic surfactant is from 0.3 to 0.9, the ratio of amphoteric surfactant is from 0.0 to 0.7, the value of 0.0 being excluded, and the ratio of nonionic surfactant is from 0.0 to 0.7, the value of 0.0 being excluded,
the pH of the composition being between 4 and 8.

According to the disclosure, the ratios and percentages indicated above can be measured by any method known to a person skilled in the art. It can concern, for example, in particular for the assaying of the anionic surfactants, the standard NF ISO 2271 (Determination of the content of anionic active materials according to a manual or mechanical method by direct titration in two phases, January 1990, AFNOR).

According to the disclosure, the anionic surfactant can be chosen from the group comprising alkyl sulfates, alkyl ether sulfates, sulfonates, phosphoric acid derivatives, phosphates and alkylphosphates and their derivatives, isethionates, taurates, sulfosuccinates, alkyl sulfoacetates, anionic derivatives of proteins of vegetable origin, amino acids and amino acid derivatives, polypeptides, carboxylic acids and their salts, salts of fatty acids resulting from saponification, lactic acid derivatives and alkyl polyglucoside derivatives.

According to the disclosure:
 the alkyl sulfates can be chosen from the group comprising sodium lauryl sulfate, sodium coco sulfate, potassium lauryl sulfate, magnesium lauryl sulfate, ammonium lauryl sulfate, triethanolamine lauryl sulfate, diethanolamine lauryl sulfate, monoethanolamine lauryl sulfate and their mixtures;
 the alkyl ether sulfates can be chosen from the group comprising sodium laureth sulfate, sodium trideceth sulfate, ammonium laureth sulfate, magnesium laureth sulfate, triethanolamine laureth sulfate, diethanolamine laureth sulfate, monoethanolamine laureth sulfate and their mixtures;
 the sulfonates can be chosen from the group comprising sodium C14-16 olefin sulfonate, sodium C14-17 sec-alkyl sulfonate and sodium xylene sulfonate, and their mixtures;
 the phosphates and alkyl phosphates can be chosen from the group comprising dicetyl phosphate, C12-15 phosphate, potassium cetyl phosphate and C9-15 alkyl phosphate, and their mixtures;
 the isethionates can be chosen from the group comprising sodium cocoyl isethionate and sodium lauroyl methyl isethionate, and their mixtures;
 the taurates can be chosen from the group comprising sodium methyl cocoyl taurate and sodium methyl stearoyl taurate, and their mixtures;
 the sulfosuccinates can be chosen from the group comprising sodium laureth sulfosuccinate, disodium undecylenamido MEA-sulfosuccinate, disodium lauryl sulfosuccinate and disodium ricinoleamido MEA-sulfosuccinate, and their mixtures;
 the alkyl sulfoacetates can be sodium lauryl sulfoacetate;
 the anionic derivatives of proteins of vegetable origin can be chosen from sodium cocoyl apple amino acids, sodium lauroyl oat amino acids, sodium lauroyl wheat amino acids and potassium lauroyl wheat amino acids, and their mixtures;
 the amino acids and derivatives of amino acids can be chosen from sodium lauroyl glutamate, sodium cocoyl glutamate, potassium cocoyl glycinate, sodium cocoyl alaninate and sodium lauroyl sarcosinate, and their mixtures;
 the carboxylic acids and their salts can be chosen from the group comprising sodium lauryl glucose carboxylate and sodium laureth-13 carboxylate, and their mixtures;
 the salts of fatty acids resulting from saponification can be chosen from the salts of lauric acid, myristic acid, palmitic acid and stearic acid, and their mixtures;

the lactic acid derivatives can be chosen from sodium stearoyl lactylate, sodium isostearyl lactylate and sodium cocoyl lactylate, and their mixtures;

the alkyl polyglucoside derivatives can be chosen from sodium cocoglucoside tartrate, disodium cocopolyglucose sulfosuccinate and disodium cocopolyglucose citrate, and their mixtures.

According to the disclosure, the at least one amphoteric surfactant can be selected from the group comprising N-alkylamidobetaines, betaines, sultaines, alkylpolyaminocarboxylates, alkylamphoacetates, their derivatives, and glycine derivatives.

According to the disclosure:

the N-alkylamidobetaines can be chosen from the group comprising cocamidopropyl betaine and lauramidopropyl betaine, and their mixtures;

the betaines can be chosen from the group comprising coco betaine and lauryl betaine, and their mixtures;

the sultaines can be cocamidopropyl hydroxysultaine, the alkylpolyaminocarboxylates can be chosen from the group comprising sodium carboxymethyl tallow polypropylamine and sodium carboxymethyl oleyl polypropylamine, and their mixtures;

the alkylamphoacetates can be chosen from the group comprising disodium cocoamphoacetate, sodium cocoamphoacetate and disodium lauroamphoacetate, and their mixtures;

the glycine derivatives can be cocoamphopolycarboxyglycinate.

According to the disclosure, at least one nonionic surfactant can be chosen from the group comprising alkyl polyglucosides, esters of glyceryl and of fatty acid, esters of sucrose and of fatty acids, oxyalkylenated esters of sucrose, oxyalkylenated esters of glycerol, esters of fatty acids and of polyethylene glycol, esters of fatty acid and of sorbitan, polyglycerolated fatty alcohols and glucamine derivatives.

According to the disclosure:

the alkyl polyglucosides can be chosen from the group comprising decyl glucoside, lauryl glucoside, caprylyl/capryl glucoside and coco glucoside, and their mixtures;

the esters of glyceryl and of fatty acid can be chosen from glyceryl stearate, glyceryl ricinoleate and glyceryl oleate, and their mixtures;

the esters of sucrose and of fatty acids can be chosen from sucrose stearate, sucrose palmitate, sucrose laurate and sucrose distearate, and their mixtures;

the oxyalkylenated esters of sucrose can be chosen from methyl glucose caprate/caprylate/oleate, PEG-120 methyl glucose dioleate and PEG-20 methyl glucose sesquistearate, and their mixtures;

the oxyalkylenated esters of glycerol can be chosen from PEG-7 glyceryl cocoate, PEG-80 glyceryl cocoate, PEG-30 glyceryl cocoate and PEG-200 hydrogenated glyceryl palmate, and their mixtures;

the esters of fatty acids and of polyethylene glycol can be chosen from the group consisting of PEG-8 stearate, PEG-20 stearate, PEG-40 stearate, PEG-50 stearate and PEG-100 stearate, and their mixtures;

the esters of fatty acid and of sorbitan can be chosen from the group comprising sorbitan palmitate, sorbitan stearate, sorbitan tristearate, sorbitan oleate and sorbitan trioleate, and their mixtures;

the glucamine derivatives can be chosen from the group consisting of capryloyl or caproyl methyl glucamide, lauroyl methyl glucamide, lauroyl methyl glucamide and cocoyl methyl glucamide, and their mixtures.

Advantageously, the anionic surfactant can be an alkyl sulfate, the amphoteric surfactant can be an N-alkylamidobetaine or an alkylamphoacetate and the nonionic surfactant can be an alkyl polyglucoside.

Advantageously, the anionic surfactant can be ammonium lauryl sulfate, the amphoteric surfactant can be cocamidopropyl betaine or sodium cocoamphoacetate and the nonionic surfactant can be decyl glucoside.

The surfactant composition according to the disclosure can constitute in particular a composition for cutaneous application, used in particular in the cosmetic or dermatological fields, such as cleansing products for the skin, including the body and the face, for the scalp and/or for the hair. A composition for topical application can optionally contain a physiologically acceptable medium, that is to say a medium compatible with the skin, mucous membranes, scalp and/or hair. It can more particularly constitute a cleansing composition for the skin.

According to the disclosure, the surfactant composition can be in a form chosen from a shower gel, a cleansing gel for the skin of the face, a shampoo and a washing gel for the hands.

According to the disclosure, the surfactant composition of the disclosure can be provided in a packaging chosen from a bottle, for example such as a bottle equipped with a cap or with a pump (metering pump or pump-action spray), a tube, for example a flexible tube, and a pot.

Advantageously, the surfactant composition of the disclosure does not comprise a preservative, this situation being favorable to better harmlessness, as indicated above.

Another subject matter of the disclosure relates to a cosmetic or dermatological composition comprising a surfactant composition according to the disclosure.

According to one embodiment, the cosmetic or dermatological composition can consist of, that is to say comprise, exclusively the surfactant composition of the disclosure.

According to the disclosure, the cosmetic composition can comprise a commercially acceptable vehicle.

Advantageously, the cosmetic composition of the disclosure has the same shear-thinning properties, and also the other advantageous properties, as the surfactant composition of the disclosure.

"Cosmetic composition" is understood to mean, in the present disclosure, any composition having a cosmetic purpose, that is to say esthetic purpose, which can be brought into contact with the surface parts of the human body, for example the epidermis, hair, including body hair, external organs and external mucous membranes. Advantageously, a cosmetic composition makes it possible, exclusively or mainly, to cleanse them, protect them or keep them in good condition.

In the present document, "dermatological composition" is understood to mean any composition having a dermatological purpose, that is to say a composition which can be brought into contact with the surface parts of the human body for treatment of the skin, mucous membranes and superficial body growths, nails or hair, including body hair.

"Cosmetically or dermatologically acceptable vehicle" is understood to mean a vehicle appropriate for use in contact with human and animal skin cells, in particular the cells of the epidermis, without toxicity, irritation, induced allergic response and the like, and proportionate to a reasonable advantage/risk ratio. The vehicle is used in proportions compatible with the high concentration of the composition of the disclosure.

According to the disclosure, the cosmetic composition of the disclosure can additionally comprise adjuvants normally used in the cosmetics field, chosen from oils, vegetable butters, vegetable or synthetic waxes, active principles, fragrances, preservatives, sequestering agents (EDTA), antioxidants, cationic polymers and cationic surfactants, pearlescent and opacifying agents, pigments, inorganic or organic fillers, such as talc, kaolin or starch, exfoliants (solid vegetable, mineral or synthetic particles having an abrasive effect on the skin), pearlescent agents and glitter, dyes, sunscreens, acids and bases for adjusting the pH, or synthetic or natural gelling polymers. The amounts of these different adjuvants are those conventionally used in the field under consideration, for example from 0.01% to 20% of the total weight of the composition. These adjuvants and also their concentrations have to be such that they do not modify the property desired for the composition of the disclosure.

Mention may be made, as an example of oil, of oils of vegetable origin, such as jojoba, avocado, sesame, sunflower, rapeseed, corn, soybean, safflower and grape seed, or mineral oils, such as liquid paraffins, or synthetic oils, such as isopropyl myristate, coco-caprylate/caprate, ethylhexyl palmitate and alkyl benzoates, or volatile or nonvolatile silicone oils, such as polydimethylsiloxanes (PDMS), cyclodimethylsiloxanes or cyclomethicones, or fluorinated or fluorosilicone oils, or alkanes of natural origin, and also mixtures of these oils. The amount of oil must not modify the property desired for the composition of the disclosure.

Mention may be made, as active principles, for example, of moisturizers, for example polyols, such as glycerol, glycols, polyethylene glycols and sugars and their derivatives, natural extracts, piroctone olamine, zinc pyrithione, salicylic acid, urea, vitamins and their derivatives (D-panthenol or tocopherol acetate, for example), protein hydrolyzates and amino acids.

The composition of the disclosure can be obtained by any appropriate process known to a person skilled in the art for the manufacture of a foaming cosmetic composition. It can, for example, be a simple mixing.

Advantageously, the composition can be a composition having a cutaneous use.

According to the disclosure, the cosmetic composition can be in a form chosen from a shower gel, a cleansing gel for the skin of the face, a shampoo, a washing gel for the hands and a household cleaning product, for example a washing-up liquid, a multiuse household cleaning gel or a household cleaning product for the floor.

Another subject matter of the disclosure relates to a cosmetic use of the cosmetic composition according to the disclosure for cleansing the skin and/or superficial body growths and/or scalp.

Another subject matter of the disclosure relates to a nontherapeutic cosmetic treatment process comprising application, to the skin and/or to superficial body growths and/or scalp, of a surfactant composition of the disclosure or of a cosmetic composition according to the disclosure.

Advantageously, the cosmetic treatment process can be a process for cleansing dirt residues from human keratinous substances (also cleansing from sweat and lipids), in which the cosmetic composition of the disclosure is applied to the skin and/or superficial body growths and/or scalp in the presence of water. Advantageously, the application can comprise a massaging in order to form a foam, which can be removed with the dirt residues by rinsing with water.

In the context of the cosmetic processes according to the disclosure or of the use according to the disclosure, the use is understood to be a nontherapeutic use, for example a use for the treatment of filthy skin, that is to say skin not exhibiting a pathological condition. Skin not exhibiting a visible or noticeable trace of an external attack, such as itching, sunburn, burns, bites/stings, signs of inflammation or signs of wounds, this list not being limiting, may also be concerned.

Preferably, any cosmetic use and any cosmetic process according to the disclosure are respectively nontherapeutic cosmetic uses and nontherapeutic cosmetic processes.

Another subject matter of the disclosure relates to a combination between a spray-generating device or a device which makes it possible to deliver a dose and a surfactant composition or a cosmetic composition according to the disclosure, in which the spray-generating device diffuses, as a spray, the cosmetic composition or the surfactant composition.

The device which makes it possible to deliver a dose can, for example, be a capsule valve, for example a capsule valve of Capsule Double Invio—ref. V143-145 type sold by the supplier Seaquist of Aptar Group.

Advantageously, the surfactant composition of the disclosure having a viscosity comparable to conventional shower gels but being shear-thinning is sprayable, that is to say that it can be dispensed by means of a spray-generating device. Without wishing to be committed to an explanation of a mechanism of action, the applicant company puts forward the hypothesis that the arrangement of the surfactants of the surfactant composition into lamellar phases makes possible the sprayability.

Advantageously, the dispensing by means of a spray-generating device of the cosmetic composition or of the surfactant composition according to the disclosure facilitates the distribution of the composition over keratinous substances, in particular facilitates the distribution of a small amount of composition (insofar as the formulation is highly concentrated) over a large surface area.

Advantageously, as the surfactant composition of the disclosure is shear-thinning, it makes possible, in combination with a spray dispensing, the ready distribution of a lower dose of product, for example 4 times lower, than with a conventional shower gel, for a surface area of keratinous substances, in particular skin, identical to or greater than that covered by a greater amount of conventional product.

The spray-generating device can be any device available on the market, for example a metering pump-action spray provided with a spray pump, for example the PZ2 190 DLD1 Helios pump (Aptar).

Other advantages may also become apparent to a person skilled in the art on reading the examples below, illustrated by the appended figures, given by way of illustration.

BRIEF DESCRIPTION OF THE FIGURES

FIG. 1 represents an X-ray photograph of a concentrated shower gel composition. The X-rays are produced by a rotating 40 kV 40 mA copper anode, with a diameter of 40 cm. The exposure time is 2 hours (8 periods of time of 15 minutes each). The sample is provided in the form of a capillary with a diameter of 1.5 mm, placed in a sample holder thermostatically controlled at 20° C. The diffraction diagram is characteristic of a lamellar phase; it consists of two thin rings (diffraction order 1 and order 2). The form of observation of FIG. 1 makes it possible to characterize the structure as nonwound planar lamellar phases.

IMPLEMENTATIONAL EXAMPLES OR EMBODIMENTS

Figure 1:
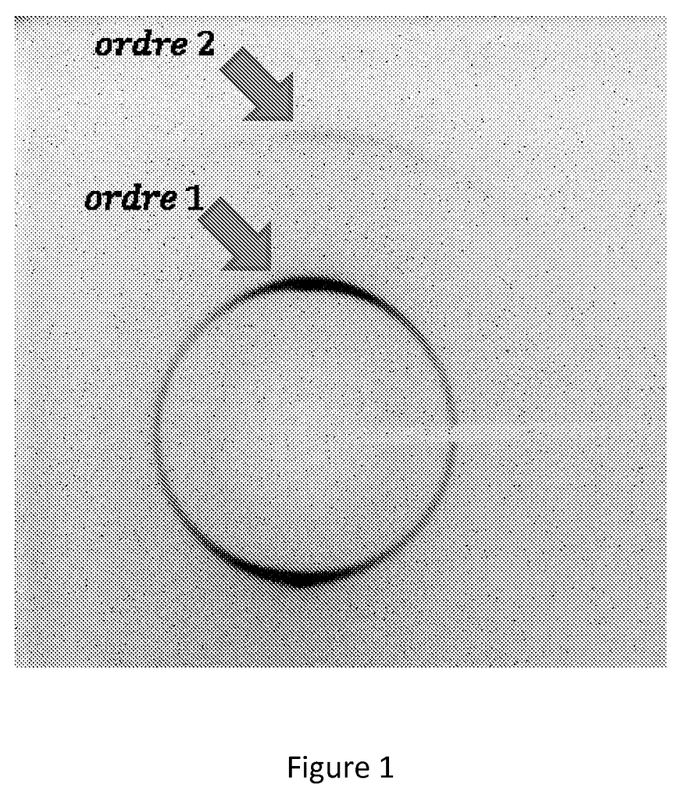
Figure 2:
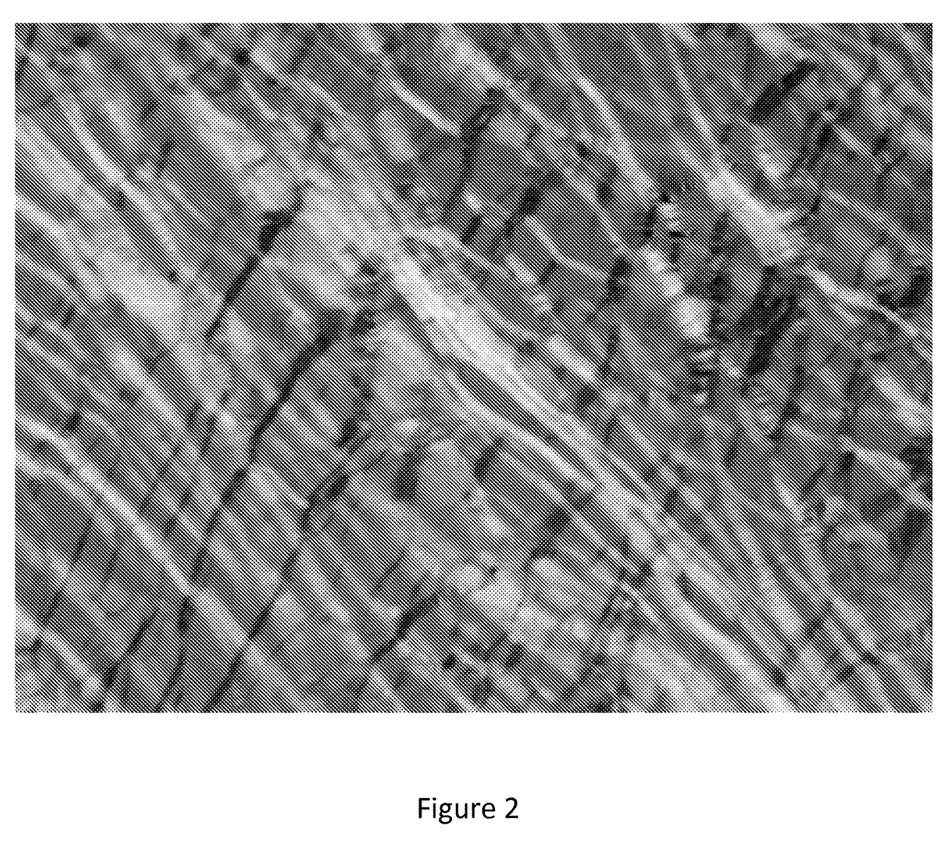
FIG. 2 represents an optical microscope photograph of the shower gel composition which is the subject of FIG. 1, in differential interference contrast.

Example 1: Process for the Preparation of a Surfactant Composition

Cocamidopropyl betaine (amphoteric surfactant) and decyl glucoside (nonionic surfactant) are added to water, at ambient temperature (approximately 20° C.). Citric acid is subsequently added to the mixture, at ambient temperature. Fragrance and then ammonium lauryl sulfate (anionic surfactant) are subsequently added to the mixture; everything is mixed at ambient temperature.

The proportions of the different components are those given in table I below:

| INCI name | Active material % |
|---|---|
| Ammonium lauryl sulfate | 25-35 |
| Cocamidopropyl betaine | 5-15 |
| Decyl glucoside | 1-5 |
| Citric acid | 0-0.5 |
| Fragrance | 1-5 |
| Water | q.s. for 100 |

Example 2: Example of a Surfactant Composition

A surfactant composition of the disclosure, with the concentrations of its components, as active material, is illustrated in table I above.

Example 3: Example of a Surfactant Composition

A surfactant composition of the disclosure, with the concentrations of its components, as active material and commercial material, is illustrated in table II below.

TABLE II

| INCI name | Active material % |
|---|---|
| Ammonium lauryl sulfate | 25-35 |
| Sodium cocoamphoacetate | 5-15 |
| Decyl glucoside | 1-5 |
| Citric acid | 0-0.5 |
| Fragrance | 1-5 |
| Water | q.s. for 100 |

This formulation is 4× concentrated, with respect to a conventional shower gel.

It is a "structured" surface-active medium: the surfactants present in the composition are arranged in a lyotropic phase of liquid crystal type; the phase is optically anisotropic and appears birefringent when it is observed in polarized light with an optical microscope. More specifically, it is a lamellar phase, where the surfactants are arranged in planar bilayers, also known as lamellae. The bilayers form a periodic stack, being separated from one another by intermediate layers of water.

Example 4: Examples of Surfactant Compositions 8 surfactant compositions of the disclosure, with the concentrations of their components, as active material and commercial material, are illustrated in table III below.

TABLE III

| INCI name | % Active material | % Active material | % Active material | % Active material | % Active material | % Active material | % Active material | % Active material |
|---|---|---|---|---|---|---|---|---|
| Ammonium lauryl sulfate | 27.2 | 30.6 | 36.0 | 23.4 | 23.4 | 19.1 | 29.0 | 25.0 |
| Sodium methyl cocoyl taurate | 0.0 | 0.0 | 0.0 | 3.6 | 0.0 | 7.2 | 0.0 | 0.0 |
| Sodium lauryl sarcosinate | 0.0 | 0.0 | 0.0 | 0.0 | 4.5 | 0.0 | 0.0 | 0.0 |
| Cocamidopropyl betaine | 0.0 | 12.6 | 12.4 | 8.1 | 8.1 | 6.6 | 10.0 | 8.6 |
| Cocoamphoacetate | 9.3 | 0.0 | 0.0 | 0.0 | 0.0 | 0.0 | 0.0 | 0.0 |
| Decyl glucoside | 2.7 | 7.6 | 3.7 | 2.3 | 2.3 | 1.9 | 2.8 | 2.4 |
| Glyceryl oleate | 0.0 | 0.0 | 0.0 | 0.8 | 0.8 | 0.6 | 0.9 | 0.8 |
| Citric acid | 2.0 | 0.0 | 0.0 | 0.2 | 0.2 | 0.2 | 0.3 | 0.2 |
| Fragrance | 2.4 | 4.7 | 4.7 | 2.4 | 2.4 | 2.4 | 3.8 | 3.3 |
| Aloe vera gel | | | | | | | 1.1 | 1.0 |
| Lemon extract | | | | | | | 0.5 | 0.5 |
| Water | | | | | | | | |

This formulation is approximately 4× concentrated, with respect to a conventional shower gel.

This formulation has the property of fluidifying on spreading.

It is a "structured" surface-active medium: the surfactants present in the composition are arranged in a lyotropic phase of liquid crystal type; the phase is optically anisotropic and appears birefringent when it is observed in polarized light with an optical microscope. More specifically, it is a lamellar phase, where the surfactants are arranged in planar bilayers, also known as lamellae. The bilayers form a periodic stack, being separated from one another by intermediate layers of water.

Example 5: Tests of Usages and of Effectivenesses of a Composition According to the Disclosure Conditions of the Tests:

In order to validate the performance and perception of the composition of the disclosure, 117 women aged between 18 and 64 years were recruited for this study. The use of the concentrated shower gel in place of the usual shower gel was carried out in a blind test at home for 7 days.

For this reason, the composition was applied once daily for 7 days under the normal conditions of use.

The overall evaluation was carried out at the first use and after 7 days of use by a grading from 0 to 10. It reflects the satisfaction with use.

The detailed evaluation was carried out after 7 days of use, with regard to the 4 descriptors: texture, fragrance, practicality of the bottle and feeling on the skin, by measurement on a scale of agreement.

The key indicators are evaluated after 7 days of use. They relate to the indicators of purchase, the recommendations, the preferences and the intention to buy and recommendation after presentation of the concept.

Results:

With regard to the overall evaluation, the results declare in favor of a very well evaluated product after a suitability time. This is because the scores progress between the 1st application (overall mean grade of 7.7) and the 7th application (overall mean grade of 8.1), with a very good evaluation of the Eco shower gel after 7 days of use. All the items progress, particularly the quality, followed by the application, by the fragrance and by the foam.

With regard to the texture, a good assessment of the texture over all the criteria (mean grade of 7.9) after 7 days of use, in particular with regard to the ease of rinsing.

The foam and the consistency are very well received after 7 days of use, both in terms of amount and of smoothness and fluidity.

The fragrance is positively evaluated (mean grade of 7.8) after 7 days of use, with clients who judge the fragrance very "pleasant, pleasing to smell" and "well suited to a shower gel", with a balanced intensity for the majority.

The evaluation of the feeling on the skin once having left the shower is good (mean grade of 8.0) after 7 days of use.

The perception of the practicality of the bottle is very good (mean grade of 8.5) after 7 days of use. The clients are very convinced by the majority of the criteria, in particular "can be taken anywhere", "remains clean, tidy", "easy to use", "the product easily comes out of the bottle".

The combined results, as percentage of clients who have responded favorably to the questions, are shown in table IV:

TABLE IV

| Criterion | Product advantage | % of clients |
| --- | --- | --- |
| Texture | Is well suited | 50 |
|  | Is pleasant to apply | 50 |
|  | Is easily rinsed off | 56 |
| Foam and consistency | Foams sufficiently | 73 |
|  | Smoothness of the foam | 74 |
|  | Fluidity of the texture | 78 |
| Fragrance | Is pleasant, which has a pleasing smell | 53 |
| Bottle | Can be taken anywhere | 76 |
|  | Remains clean, tidy (product does not fall) | 75 |
|  | The product easily comes out of the bottle | 68 |
|  | Makes it possible to save space in my bathroom | 59 |
|  | Easy to use | 69 |

The comparison with a usual shower gel reflects an advantage for the product of the disclosure with regard to the majority of the criteria, in particular with regard to the texture, with respect to the skin, suitable for all the family and logically with regard to the practicality, as shown in table V:

TABLE V

| Product advantage | Usual shower gel | Test shower gel |
| --- | --- | --- |
| It is pleasant to use | 11 | 18 |
| Is of quality | 10 | 18 |
| Has a pleasant texture | 7 | 26 |
| Spreads easily on the skin | 18 | 23 |
| Is easily rinsed off | 9 | 13 |
| Foams sufficiently | 23 | 31 |
| The fragrance is pleasant | 28 | 35 |
| Practical to carry | 21 | 26 |
| The bottle is practical | 1 | 74 |
| The product easily comes out of the bottle | 2 | 62 |
| Washes my skin gently | 7 | 40 |
| Leaves the skin soft | 8 | 27 |
| Respects the balance of the skin | 14 | 25 |
| Does not dry out the skin | 11 | 22 |
| Suitable for my personal use | 17 | 25 |
| Suitable for all the family | 9 | 22 |

In conclusion, more than half the respondents would use the test shower gel every day in place of their usual shower gel.

Example 6: Tests of Use Under Dermatological Monitoring of the Vanilla-Fragrance Eco Shower Gel The aim of the study was:

(1) to confirm the cutaneous tolerance of vanilla-fragrance Eco shower gels (containing the composition of the disclosure) applied under normal conditions of use, (2) to assess the cosmetic qualities and also the overall satisfaction of the vanilla Eco shower gels applied under normal conditions of use, and (3) to evaluate the mean amount used for the vanilla Eco shower gels, applied by the volunteers under normal conditions of use.

Protocol of the Study

The product studied was applied to the body at least once daily, for 3 consecutive weeks, by 27 healthy adult volunteers.

These applications were carried out by the volunteer herself, at her home and according to the protocol of use described by the promoter.

The product studied was used in place of the product of the same type which the volunteer normally or occasionally uses.

Mode of application: A knob of formulation is sufficient on wet skin.

=a single pressing per shower (the produce is concentrated)

To be spread over the whole of your body, in place of your conventional shower gel.

At T0:

The bottles are weighed before starting the test.

The volunteers arrive without having applied cosmetic product to the body on the day of the appointment.

Clinical examination and confirmation of the criteria for inclusion and non-inclusion by the doctor.

From T0 to T3 weeks:

The volunteers apply the study product at home and under the normal conditions of use of the product, in place of that usually used, and according to the instructions mentioned in the questionnaire (frequency and duration of use, region and mode of application).

The volunteers evaluate the cosmetic qualities of the product, the assertions and overall satisfaction.

The volunteers must not use new cosmetic products (with the exception of that of the study).

The volunteers must not change their habits of use of cosmetic products other than the product having the same effects as the test product.

At T3 weeks:

The volunteers arrive for consultation without having applied cosmetic product to the body on the day of the appointment.

Clinical examination with a doctor, who also confirms that the protocol has been well observed.

The volunteers hand over the evaluation questionnaire and the test product.

The bottles recovered are weighed.

Monitoring of the Study 27 adult volunteers were recruited for the vanilla product. No subject was excluded from the studies. The characteristics of the volunteers are mentioned in table VI.

TABLE VI

CHARACTERISTICS OF THE VOLUNTEERS - VANILLA ECO SHOWER GEL 27 SUBJECTS

| Age mean of the study: (min. age: 31 years; max. age: 72 years) Skin type: | 56 years |
|---|---|
| Very dry | 7% |
| Dry | 70% |
| Normal | 22% |

Results and Discussion: Assessment of the Skin Tolerance

For 55.5% of the volunteers, the possible clinical signs (dryness) present as D0 have disappeared, showing improvement in the skin condition, or have not changed. These volunteers did not note any skin reaction or functional sign related to the use of the test vanilla Eco shower gel and judged the tolerance to be excellent.

For 40.8% of the volunteers, no clinical sign was observed at D0, as at D21. These volunteers did not note any skin reaction or functional sign relating to the use of the test vanilla Eco shower gel and judged the tolerance to be excellent.

In the light of these comments and of the very good tolerance with the majority of the volunteers, the overall tolerance is judged to be good.

Example 7: Tests of Use Under Dermatological Monitoring of the Olive-Fragrance Eco Shower Gel The aim of the study was:

(1) to confirm the cutaneous tolerance of olive-fragrance Eco shower gels (containing the composition of the disclosure) applied under normal conditions of use, (2) to assess the cosmetic qualities and also the overall satisfaction of the olive Eco shower gels applied under normal conditions of use, and (3) to evaluate the mean amount used for the olive Eco shower gels, applied by the volunteers under normal conditions of use.

Protocol of the Study

The product studied was applied to the body at least once daily, for 3 consecutive weeks, by 26 healthy adult volunteers.

These applications were carried out by the volunteer herself, at her home and according to the protocol of use described by the promoter.

The product studied was used in place of the product of the same type which the volunteer normally or occasionally uses.

Mode of application: A knob of formulation is sufficient on wet skin.

=a single pressing per shower (the produce is concentrated)

To be spread over the whole of your body, in place of your conventional shower gel.

At T0:

The bottles are weighed before starting the test.

The volunteers arrive without having applied cosmetic product to the body on the day of the appointment.

Clinical examination and confirmation of the criteria for inclusion and non-inclusion by the doctor.

From T0 to T3 Weeks:

The volunteers apply the study product at home and under the normal conditions of use of the product, in place of that usually used, and according to the instructions mentioned in the questionnaire (frequency and duration of use, region and mode of application).

The volunteers evaluate the cosmetic qualities of the product, the assertions and overall satisfaction.

The volunteers must not use new cosmetic products (with the exception of that of the study).

The volunteers must not change their habits of use of cosmetic products other than the product having the same effects as the test product.

At T3 Weeks:

The volunteers arrive for consultation without having applied cosmetic product to the body on the day of the appointment.

Clinical examination with a doctor, who also confirms that the protocol has been well observed.

The volunteers hand over the evaluation questionnaire and the test product.

The bottles recovered are weighed.

Monitoring of the Study 26 adult volunteers were recruited for the olive product. No subject was excluded from the studies. The characteristics of the volunteers are mentioned in table VII.

TABLE VII

CHARACTERISTICS OF THE VOLUNTEERS - VANILLA ECO SHOWER GEL 26 SUBJECTS

| Age mean of the study: (min. age: 27 years; max. age: 60 years) Skin type: | 47 years |
|---|---|
| Very dry | 4% |
| Dry | 81% |
| Normal | 15% |

Results and Discussion: Assessment of the Skin Tolerance

For 65.4% of the volunteers, the possible clinical signs (dryness) present as D0 have disappeared, showing improvement in the skin condition, or have not changed. These volunteers did not note any skin reaction or functional sign related to the use of the test olive Eco shower gel and judged the tolerance to be excellent.

For 19.2% of the volunteers, no clinical sign was observed at D0, as at D21. These volunteers did not note any skin reaction or functional sign relating to the use of the test olive Eco shower gel and judged the tolerance to be excellent.

In the light of these comments and of the very good tolerance with the majority of the volunteers, the overall tolerance is judged to be good.

Example 8: Tests of Use Under Dermatological Monitoring of the Mango-Fragrance Eco Shower Gel The aim of the study was:

(1) to confirm the cutaneous tolerance of mango-fragrance Eco shower gels (containing the composition of the disclosure) applied under normal conditions of use, (2) to assess the cosmetic qualities and also the overall satisfaction of the mango Eco shower gels applied under normal conditions of use, and (3) to evaluate the mean amount used for the mango Eco shower gels, applied by the volunteers under normal conditions of use.

Protocol of the Study

The product studied was applied to the body at least once daily, for 3 consecutive weeks, by 27 healthy adult volunteers.

These applications were carried out by the volunteer herself, at her home and according to the protocol of use described by the promoter.

The product studied was used in place of the product of the same type which the volunteer normally or occasionally uses.

Mode of application: A knob of formulation is sufficient on wet skin.

=a single pressing per shower (the produce is concentrated) To be spread over the whole of your body, in place of your conventional shower gel.

At T0:

The bottles are weighed before starting the test.

The volunteers arrive without having applied cosmetic product to the body on the day of the appointment.

Clinical examination and confirmation of the criteria for inclusion and non-inclusion by the doctor.

From T0 to T3 Weeks:

The volunteers apply the study product at home and under the normal conditions of use of the product, in place of that usually used, and according to the instructions mentioned in the questionnaire (frequency and duration of use, region and mode of application).

The volunteers evaluate the cosmetic qualities of the product, the assertions and overall satisfaction.

The volunteers must not use new cosmetic products (with the exception of that of the study).

The volunteers must not change their habits of use of cosmetic products other than the product having the same effects as the test product.

At T3 Weeks:

The volunteers arrive for consultation without having applied cosmetic product to the body on the day of the appointment.

Clinical examination with a doctor, who also confirms that the protocol has been well observed.

The volunteers hand over the evaluation questionnaire and the test product.

The bottles recovered are weighed.

Monitoring of the Study 27 adult volunteers were recruited for the mango product. No subject was excluded from the studies. The characteristics of the volunteers are mentioned in table VIII.

TABLE VIII

CHARACTERISTICS OF THE VOLUNTEERS - MANGO ECO SHOWER GEL 27 SUBJECTS

| | |
|---|---|
| Age mean of the study: (min. age: 27 years; max. age: 74 years) Skin type: | 56 years |
| Very dry | 7% |
| Dry | 78% |
| Normal | 15% |

Results and Discussion: Assessment of the Skin Tolerance

For 59.3% of the volunteers, the possible clinical signs (dryness) present as D0 have disappeared, showing improvement in the skin condition, or have not changed. These volunteers did not note any skin reaction or functional sign related to the use of the test mango Eco shower gel and judged the tolerance to be excellent.

For 37.0% of the volunteers, no clinical sign was observed at D0, as at D21. These volunteers did not note any skin reaction or functional sign relating to the use of the test mango Eco shower gel and judged the tolerance to be excellent.

In the light of these comments and of the very good tolerance with the majority of the volunteers, the overall tolerance is judged to be good.

The invention claimed is:

1. A shear-thinning surfactant composition structured into planar lamellar phases consisting of:
   a) at least one anionic surfactant,
   b) at least one compound chosen from amphoteric surfactants and nonionic surfactants,
   c) optionally fragrance,
   d) an acid or base for adjusting the pH, and
   e) water,
   in which the total active material of said surfactants is from 35% to 60% by weight, with respect to the total weight of said composition,
   in which the ratio of anionic surfactant is from 0.4 to 0.8, the ratio of amphoteric surfactant is from 0.2 to 0.5 and the ratio of nonionic surfactant is from 0.0 to 0.1, said ratio being the ratio of the percentage by weight of active material of said surfactant in said composition to the percentage by weight of total active material of said surfactants in said composition,
   the pH of the composition being between 4 and 8,
   said at least one anionic surfactant is ammonium lauryl sulfate, and the shear-thinning surfactant composition is a sprayable gel,
   wherein the fragrance, when present, ranges from 0.05% to 10% by weight, with respect to the total weight of said composition, and
   in which water is from 40% to 65% by weight, with respect to the total weight of said composition.

2. The composition as claimed in claim 1, in which said at least one amphoteric surfactant is selected from the group consisting of N-alkylamidobetaines, betaines, sultaines, alkylpolyaminocarboxylates, alkylamphoacetates and cocoamphopolycarboxyglycinate.

3. The composition as claimed in claim 2, in which:
   said N-alkylamidobetaines are selected from the group consisting of cocamidopropyl betaine and lauramidopropyl betaine, and their mixtures;
   said betaines are selected from the group consisting of coco betaine and lauryl betaine, and their mixtures;

said sultaines is cocamidopropyl hydroxysultaine,
said alkylpolyaminocarboxylates are selected from the group consisting of sodium carboxymethyl tallow polypropylamine and sodium carboxymethyl oleyl polypropylamine, and their mixtures:
said alkylamphoacetates are selected from the group consisting of disodium cocoamphoacetate, sodium cocoamphoacetate and disodium lauroamphoacetate, and their mixtures.

4. The composition as claimed in claim 1, in which said at least one nonionic surfactant is selected from the group consisting of alkyl polyglucosides, esters of glyceryl and of fatty acid, esters of sucrose and of fatty acids, oxyalkylenated esters of sucrose, oxyalkylenated esters of glycerol, esters of fatty acids and of polyethylene glycol, esters of fatty acid and of sorbitan, polyglycerolated fatty alcohols and glucamine derivatives selected from the group consisting of capryloyl or caproyl methyl glucamide, lauroyl methyl glucamide, lauroyl methyl glucamide and cocoyl methyl glucamide, and their mixtures.

5. The composition as claimed in claim 4, in which:
said alkyl polyglucosides are selected chosen from the group consisting of decyl glucoside, lauryl glucoside, caprylyl/capryl glucoside and coco glucoside, and their mixtures;
said esters of glyceryl and of fatty acid are selected from the group consisting of glyceryl stearate, glyceryl ricinoleate and glyceryl oleate, and their mixtures;
the esters of sucrose and of fatty acids are selected from the group consisting of sucrose stearate, sucrose palmitate, sucrose laurate and sucrose distearate, and their mixtures;
the oxyalkylenated esters of sucrose are selected from the group consisting of methyl glucose caprate/caprylate/oleate, PEG-120 methyl glucose dioleate and PEG-20 methyl glucose sesquistearate, and their mixtures;
the oxyalkylenated esters of glycerol are selected from the group consisting of PEG-7 glyceryl cocoate, PEG-80 glyceryl cocoate, PEG-30 glyceryl cocoate and PEG-200 hydrogenated glyceryl palmate, and their mixtures;
said esters of fatty acids and of polyethylene glycol are selected from the group consisting of PEG-8 stearate, PEG-20 stearate, PEG-40 stearate, PEG-50 stearate and PEG-100 stearate, and their mixtures; and
said esters of fatty acid and of sorbitan are selected from the group consisting of sorbitan palmitate, sorbitan stearate, sorbitan tristearate, sorbitan oleate and sorbitan trioleate, and their mixtures.

6. The composition as claimed in claim 1, in which said anionic surfactant is ammonium lauryl sulfate, the amphoteric surfactant is an N-alkylaminobetaine or an alkylamphoacetate and the nonionic surfactant is an alkyl polyglucoside.

7. The composition as claimed in claim 1, in which said anionic surfactant is ammonium lauryl sulfate, the amphoteric surfactant is cocamidopropyl betaine or sodium cocoamphoacetate and the nonionic surfactant is decyl glucoside.

8. The composition as claimed in claim 1, wherein said fragrance is present.

9. A cosmetic or dermatological composition, or a household cleaning product, comprising a surfactant composition as defined according to claim 1.

10. The composition as defined in claim 9, wherein said composition is a shower gel, a cleansing gel for the skin of the face, a shampoo, or a washing gel for the hands.

11. The product as defined in claim 10, wherein the product is a washing-up liquid, a multiuse household cleaning gel, or a household cleaning product for the floor.

12. A cosmetic treatment process comprising cleansing the skin and/or superficial body growths with the cosmetic composition as defined in claim 9.

13. A combination between a spray-generating device and a surfactant composition as defined in claim 1, in which said spray-generating device diffuses, as a spray, said cosmetic composition.

* * * * *